United States Patent
Moro

(10) Patent No.: US 6,514,685 B1
(45) Date of Patent: *Feb. 4, 2003

(54) DETECTION OF CANCER USING ANTIBODIES TO THE ALPHAFETO PROTEIN RECEPTOR

(76) Inventor: Ricardo J. Moro, 1007-1625 W. 13th Avenue, Vancouver (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/920,654

(22) Filed: Aug. 15, 1997

Related U.S. Application Data

(63) Continuation of application No. 08/308,141, filed on Sep. 19, 1994, now abandoned.

(51) Int. Cl.$^7$ .......................... C12Q 1/00; G01N 33/53; G01N 33/567; G01N 1/30
(52) U.S. Cl. ..................... 435/4; 435/7.1; 435/7.21; 435/40.5; 435/7.23; 435/7.7; 435/7.9; 435/40.51; 435/40.52
(58) Field of Search .................. 435/7.1, 7.8, 40.5, 435/4, 7.21, 7.23, 7.7, 7.9, 40.51, 40.52; 530/391.1; 424/1.11, 9.34

(56) References Cited

PUBLICATIONS

Scaver, S.S. Genetic Engineering News 14(14):10&21, Aug. 1994.*
Moro, R. et al. Tumor Biol. 14:116–130, Aug. 1993.*
Harlow and Lane, "Antibodies: A Laboratory Manual" Cold Spring Harbor Press, pp. 92–123, 142, 342 and 343, 1988.*
DePalatis, L.R. et al. Laboratory Investigation 65(1):111–120, 1991.*
O'Daly, J.P. et al. Enzyme Microb. Technol. 14:299–302, 1992.*
Hirai, H. Acta Radiologica Supplementum 374:57–64, 1990.*
Torres, J–M. et al. Biochimica et Biophysica Acta 1159:60–66, 1992.*
Esteban, C. et al. Int. J. Cancer 49:425–430, 1991.*
Toran–Allerand, C.D. Developmental Brain Research 5:213–217, 1982.*
Derner (Bio/Technology, 12:320), 1994.*
Freshney (Culture of Animal Cells, A Manual of Basic Technique, Alan R. Liss, Inc., New York, p. 4), 1994.*
Wang et al (Life Sci., 64:1, 17–23), 1999.*

* cited by examiner

Primary Examiner—Susan Ungar

(57) ABSTRACT

A method for detecting cancer in a patient. The method comprises the steps of introducing labeled antibodies or labeled AFP to a biological sample of the patient so the labeled antibodies or labeled AFP will react with the AFP receptor binding sites in the biological sample. Next there is the step of identifying AFP receptor binding sites in the biological material which are reacted with the labeled antibodies or labeled AFP to determine the presence of cancer.

17 Claims, 10 Drawing Sheets

DETECTION OF CANCER USING ANTIBODIES TO THE ALPHAFETO PROTEIN RECEPTOR

This application is a continuation of application Ser. No. 08/308,141 filed Sep. 19, 1994, now abandoned.

FIELD OF THE INVENTION

The present invention is related to the detection and/or treatment of cancer. More specifically, the present invention utilizes the existence of AFP receptor as a basis to detect cancer or contain or eliminate cancer in a patient.

BACKGROUND OF THE INVENTION

Twenty years ago, Abelev et al. reported the existence of the first oncofetal antigen, alphafetoprotein (AFP) [Abelev, G. I., Perova, S. D., Khramkova, N. I., Postnikova, Z. A. and Irlin, I. S., Transplantation 1, 174 (1963)]. Although this is the major circulating protein during fetal life, it almost disappears after birth, its normal adult serum concentration being less than 50 ng/ml [Ruoslahti, E. and Seppals, M., Int. J. Cancer 8, 374 (1971)]. However, in certain malignant diseases such as hepatocarcinomas or teratocarcinomas, plasma levels can be one thousand-fold higher [Ruoslahti, E. and Seppals, M. Adv. Cancer Res. 29, 275 (1979)]. This finding not only drew the attention of clinicians, who envisaged a new means for detecting malignancy and monitoring cancer patients, but also the interest of investigators studying the physiology of that protein during fetal life.

One of the first parameters studied was AFP distribution within the embryo. Using immunoperoxidase methods, Benno and Williams described the distribution of AFP in the developing rat brain [Benno, R. H. and Williams, T. H., Brain Res. 142, 1982 (1978)]. Shortly thereafter, a series of papers reported the localization of plasma proteins within developing nervous cells in several species including birds and man [Trojan, J. and Uriel, J., J. Oncodevelop. Biol. Med. 1, 107 (1980); Uriel, J., Trojan, J., Dubouch, P. and Pieiro, A., Path. Biol. 30, 79 (1982); Moro, R. and Uriel, J., J. Oncodevelop. Biol. Med. 2, 391 (1981); Dziegielewska, K. M., Evans, C. A. N., Lorscheider, E. L., Malinowska, D. H., Mollgard, K., Reynolds, M. L. and Saunders, N. R., J. Physiol. 318, 239 (1981); Mollgard, K., Jacobsen, M., Krag-Jacobsen, G., Praetorius-Claussen, P. and Saunders, N. R., Neurosci. Lett. 14, 85 (1979)]. For a given tissue or organ, the kinetics of the staining for AFP and serum albumin (SA) follow a rather constant pattern across different species [Uriel, J., Trojan, J., Moro, R. and Pieiro, A., Ann. N.Y. Acad. Sci. 417, 321 (1983)]. When a nervous structure is very immature, no intracellular AFP or SA is detected. Then, suddenly, and for a certain period of time depending upon the species, both proteins are simultaneously observed, even within the same cell [Torand-Allerand, C. D., Nature 286, 733 (1980)]. Subsequently, staining intensity fades and positive cells become scarce, first for AFP and later for SA. Mature structures are negative for both proteins. Other serum constituents, such as IgG, or ovalbumin in chicken embryos, are never found during fetal life within neural cells, in spite of being present in the cerebrospinal fluid [Fielitz, W., Esteves, A. and Moro, R., Dev. Brain Res. 13, 111 (1984)].

Incorporation of AFP by Embryonic Cells

One question arising from these initial observations was whether AFP and SA were incorporated from extracellular sources or synthesized in-situ. While it is not yet clear if neural cells are capable of synthesizing plasma proteins [Ali, M., Raul, H. and Sahib, M., Dev. Brain Res. 1, 618 (1981); Ali, M., Mujoo, K. and Sahib, M., Dev. Brain Res. 6, 47 (1983); Schachter, B. S. and Toran-Allerand, C. D., Dev. Brain Res. 5, 95 (1982); Pieiro, A., Calvo, M., Iguaz, F., Lampreave, F. and Naval, J. Int. J. Biochem. 14, 817 (1982)], it has been demonstrated, both in-vitro [Uriel, J., Faivre-Bauman, A., Trojan, J. and Foiret, D. Neurosci. Lett. 27, 171 (1981); Hajeri-Germond, M., Trojan, Uriel, J. and Hauw, J. J. Dev. Neurosci. 6, 111 (1984)] and in-vivo [Villacampa, M. J., Lampreave, F., Calvo, M., Pieiro, A. and Uriel, J. Dev. Brain Res. 12, 77 (1984); Moro, R., Fielitz, W., Grunberg, J. and Uriel, J., Int. J. Dev. Neurosci. 2, 143 (1984)], that neuroblasts can readily incorporate AFP and serum albumin from extracellular sources. The in-vivo experiments were done with homologous and with heterologous proteins. In the first case [Villacampa, M. J., Lampreave, F., Calvo, M., Pieiro, A. and Uriel, J. Dev. Brain Res. 12, 77 (1984)], it was shown that upon injection into pregnant rats, 125I-AFP localized in the fetal brain, as well as in other fetal organs such as the gut, skin, and tongue, organs in which native intracellular AFP had been previously reported [Trojan, J. and Uriel, J., Oncodev. Biol. Med. 3, 13 (1982)]. The second set of experiments [Moro, R., Fielitz, W., Grunberg, J. and Uriel, J., Int. J. Dev. Neurosci. 2, 143 (1984)] showed that when newborn rat serum was injected into the mesencephalic cavity of chicken embryos, rat AFP and rat SA could be detected in the same location as their native counterparts. This also indicated that AFP and SA from one species are taken up by cells from another species, thus pointing to structures and mechanisms conserved throughout evolution. This, in turn, suggests a basic biological principle is involved.

In spite of the high concentration of rat IgG injected, the staining for this protein was negative. This is not the result of its high molecular weight (150,000) which could hinder a passive diffusion, since ovalbumin (MW=43,000) could not be detected either, even when injected at twofold the normal molar concentration of AFP in the embryonic cerebrospinal fluid [Fielitz, W., Esteves, A. and Moro, R., Dev. Brain Res. 13, 111 (1984)]. This selectivity favoured the hypothesis of a specific receptor mediated mechanism of endocytosis [Moro, R. and Uriel, J., J. Oncodevelop. Biol. Med. 2, 391 (1981); Moro, R., Fielitz, W., Grunberg, J. and Uriel, J., Int. J. Dev. Neurosci. 2, 143 (1984)].

AFP Incorporation Depends on Cell Differentiation

However, at this point it was still unclear whether the uptake of AFP and SA was a cell-dependent phenomenon, or if the staining disappeared as a result of low extracellular protein availability due to the closing of the brain-blood barrier or to the low concentration of circulating AFP at the end of fetal life. It was demonstrated, first in chicken [Moro, R., Neurosci. Lett. 41, 253 (1983)] and then in human embryos [Jacobsen, M., Lassen, L. C. and Mollgard, K., Tumor Biol. 5, 55 (1984)], that spinal ganglion neural cells accomplish the entire negative-positive-negative staining cycle for AFP before its highest peak in serum is attained. Moreover, when AFP becomes undetectable, SA continues to be present for some time, thus indicating that these serum proteins have access to the ganglionic neuroblasts.

AFP Receptors in Immature Cells

The cellular uptake of AFP suggests the existence of a specific receptor whose expression is regulated according to the degree of cell differentiation [[Uriel, J., Trojan, J., Moro, R. and Pieiro, A., Ann. N.Y. Acad. Sci. 417, 321 (1983); Moro, R., Neurosci. Lett. 41, 253 (1983)]. A previous report [Uriel, J., Bouillon, D., Russel, C. and Dupiers, M., Proc. Nat. Acad. Sci. U.S.A. 73, 1452 (1976)] showed the presence of two ultracentrifugation fractions containing AFP in immature rat uterine cytosols; a 4s fraction, corresponding entirely to AFP, and an 8s fraction in which the immunological detection of AFP was only possible after treatment with 0.4 M KCI. This treatment transformed the 8s fraction into the 4s one. Very likely the 8s fraction corresponded to a receptor-AFP complex, which was dissociated at high KC1 concentrations, even though at the time the AFP receptor concept was not born yet. This dissociation of the AFP-receptor complex with KC1 was also observed by Smalley and Sarcione [Smalley, J. R. and Sarcione, E. J. Bioch. Biohys. Res. Comm. 94, 1429 (1980)] who also provided evidence that the AFP molecule could be synthesized by immature rat uterus cells.

Expression of the AFP Receptor in Cancer Cells

Since cancer cells share a number of common biochemical and antigenical features with fetal cells [Uriel, J., Adv. Cancer Res. 29, 127 (1979)], it is possible that malignant cells, derived from tissues which incorporate AFP during fetal life, might reexpress the corresponding receptor and thus take up AFP again. In support of this hypothesis, Sarcione et al., [Sarcione, E. J., Zloty, M., Delluomo, D. S., Mizejewski, G. and Jacobson, H., Cancer Res. 43, 3739 (1983)] found AFP in an 8s complex derived from human mammary carcinomas which could be dissociated by KC1 treatment in the same way as in the experiments using immature rat cytosols. More recently, these authors have demonstrated that AFP is synthesized by the MCF-7 human breast cancer cell line as a complex which needs to be dissociated in order to make AFP immunologically detectable [Sarcione, E. J. and Hart, D., Int. J. Cancer 35, 315 (1985)]. On the other hand, this cell line [Uriel, J., Failly-Crepin, C., Villacampa, M. J., Pieiro, A., and Geuskens, M., Tumor Biol. 5, 41 (1984)], and a nickel induced rat rhabdomyosarcoma [Uriel, J., Poupon, M. F. and Geuskens, M., Br. J. Cancer 48, 263 (1983)] were shown to take up AFP in vitro. As a confirmation of these indirect results, surface receptors for AFP were detected on the MCF-7 line [Villacampa, M. J., Moro, R., Naval, J., Failly-Crpin, Ch., Lampreave, F. and Uriel, J., Bioch. Biophys. Res. Commun. 122, 1322 (1984)]. The binding parameters point to a two-site receptor model exhibiting positive cooperation. The high affinity site has a Kd of $1.5 \times 10^{-9}$ M with an exhibiting positive cooperation. The high affinity site has a Kd of $1.5 \times 10^{-9}$ M with an n-2,000/cell. The low affinity site, present at 320,000/cell has a Kd of $2.2 \times 10^{-7}$ M. Later studies showed the presence of a similar receptor system on the surface of mouse YACT lymphoma cells, which is absent from normal adult mouse T cells [Naval, J., Villacampa, M. J., Goguel, A. F. and Uriel, J. Proc. Natl. Acad. Sci. U.S.A. 82, 3301 (1985)].

These studies were done in parallel with in-vivo experiments in which mice bearing spontaneous mammary tumors were injected with radioiodinated AFP. The tissue distribution of radioactivity showed a tumor/normal tissue (liver) ratio of 3.6 [Uriel, J., Villacampa, M. J., Moro, R., Naval, J. and Failly-Crpin, CH. C.R. Acad. Sci. (Paris) 297, 589 (1983); Uriel, J., Villacampa, M. J., Moro, R., Naval, J. and Failly-Crpin, C., Cancer Res. 44, 5314 (1984)]. Autoradiography of tumor sections from these animals showed a significant accumulation of silver grains around the nuclear membrane of malignant cells but not of normal cells [Uriel, J., Villacampa, M. J., Moro, R., Naval, J. and Failly-Crpin, C., Cancer Res. 44, 5314 (1984)].

Scintigraphic Imaging of Mouse Tumors Using 131I-AFP

Using $^{131}$I-AFP, positive scintigraphic images of mouse mammary tumors as small as 3–4 mm have been obtained [Uriel, J., Villacampa, M. J., Moro, R., Naval, J. and Failly-Crpin, C., Cancer Res. 44, 5314 (1984); Moro, R., Heuguerot, C., Vercelli-Retta, J., Fielitz, W., Lpez, J. J. and Roca, R., Nuclear Med. Comm. 5, 5 (1984)]. In fact, eleven out of twelve such tumors were detectable with a standard gamma camera linked to a computer. Another mouse tumor, a neuroblastoma, could also be scanned in a similar manner [Hajeri-Germond, M., Naval, J., Trojan, J. and Uriel, J., Br. J. Cancer 51, 791 (1985)].

The expression of AFP uptake or direct evidence for the AFP receptor has been shown in several different types of tumors some of which are: A rat rhabdomyosarcoma [Uriel, J., Poupon, M. F. and Geuskens, M., Br. J. Cancer 48, 263 (1983)], a mouse neuroblastoma [Hajeri-Germond, M., Naval, J., Trojan, J. and Uriel, J., Br. J. Cancer 51, 791 (1985)], mouse and human mammary carcinomas [Villacampa, M. J., Moro, R., Naval, J., Failly-Crpin, Ch., Lampreave, F. and Uriel, J., Bioch. Biophys. Res. Commun. 122, 1322 (1984); Naval, J., Villacampa, M. J., Goguel, A. F. and Uriel, J. Proc. Natl. Acad. Sci. U.S.A. 82, 3301 (1985); Uriel, J., Villacampa, M. J., Moro, R., Naval, J. and Failly-Crpin, CH. C.R. Acad. Sci. (Paris) 297, 589 (1983); Uriel, J., Villacampa, M. J., Moro, R., Naval, J. and Failly-Crpin, C., Cancer Res. 44, 5314 (1984); Moro, R., Heuguerot, C., Vercelli-Retta, J., Fielitz, W., Lpez, J. J. and Roca, R., Nuclear Med. Comm. 5, 5 (1984); Biddle, W. and Sarcione, E. J., Breast Cancer Res. Treat. 10, 281 (1987)] mouse T lymphomas [Naval, J., Villacampa, M. J., Goguel, A. F. and Uriel, J. Proc. Natl. Acad. Sci. U.S.A. 82, 3301 (1985), human T and B cell lymphomas [Laborda, J., Naval, J., Allouche, M., Calvo, M., Georgoulias, V., Mishal, Z. and Uriel, J. Int J. Cancer 40, 314 (1987); Calvo, M., Laborda, J., Naval, J., Georgoulias, V. and Uriel, J., presented at the XIII Meeting of the ISOBM (Paris 1985); Torres, J. M., Anel, A., and Uriel, J., J. Cell Physiol. 150, 458 (1992); Torres, J. M., Gueskens, M. and Uriel, J., Int. J. Cancer 47, 112 (1991)] as well as phittohemaglutinin activated human T lymphocytes [Torres, J. M., Laborda, J., Naval, J., Darracq, N., Calvo, M., Mishal, Z. and Uriel, J. Mol. Immunology 26, 851 (1989)], the human malignant monocyte cell line U937 [Suzuki, Y., Zeng, C. Q., Alpert, E. J. Clinic. Invest. 90, 1530 (1992)] and the HT29 human colon carcinoma cell line [Esteban, C., Gueskens, M. and Uriel, J., Int. J. Cancer 49, 425 (1991)].

These findings place the AFP receptor as a widespread oncofetal antigen, related to the malignant state rather than the tumor type.

Monoclonal Antibodies Against the AFP Receptor

Labeled AFP (FITC, radioactive tracers) does not bind to tumor cells on paraffin tissue sections, probably due to the partial denaturation of the receptor's binding site during fixation and to the relatively low affinity it exhibits towards its receptor. Thus, monoclonal antibodies (Mabs) against the AFP receptor were produced using a pool of human mammary carcinomas as the immunogen [Moro, R., Tamaoki, T., Wegmann, T. G., Longenecker, B. M., and Laderoute, M. P. Tumour Biol. 14, 116 (1993), incorporated by reference].

Two IgM producing Mabs recognize a 67 KD double band on PAGE gels under non-reducing conditions. The 67 KD bands are also reactive with $^{125}$I-AFP. These Mabs react with the binding site of the AFP receptor, since they inhibit the binding of AFP to tumor cells, and conversely they are inhibited from binding to the cells in the presence of a large excess of AFP. The Mabs do not react with AFP. They recognize fetal cells and mammary carcinomas on tissue sections, but not mammary adenomas or most other normal adult tissues.

During the last decades, scientists have been trying to characterize antigens related to malignancy. The AFP receptor, which should be considered as an oncofetal antigen could fulfill many of the requirements of a clinically useful tumor marker. Further work using monoclonal antibodies against this widespread cancer related antigen will allow one to determine their clinical usefulness as well as to study the physiological role of the AFP receptor.

SUMMARY OF THE INVENTION

The present invention pertains to a method for detecting cancer in a patient. The method comprises the steps of introducing labeled antibodies or labeled AFP to a biological sample of the patient so the labeled antibodies or labeled AFP will react with the AFP receptor binding sites in the biological sample. Next there is the step of identifying AFP receptor binding sites in the biological material which are reacted with the labeled antibodies or labeled AFP to determine the presence of cancer. Preferably, before the introducing step, there is the step of obtaining a biological sample from a body of a patient.

The present invention pertains to a method for treating cancer cells in a patient. The method comprises the steps of introducing AFP receptor antibodies to cancer cells in the patient. Then there is the step of reacting the AFP receptor antibodies with the AFP receptor of the cancer cells to inhibit growth of the cancer cells or kill the cancer cells.

The present invention pertains to a method for monitoring a patient. The method comprises the steps of treating the patient for cancer. Then there is the step of testing the patient at predetermined intervals after the treatment for AFP receptor site levels.

The present invention pertains to a method for treating a patient. The method comprises the steps of testing the patient for AFP receptor. Then there is the step of introducing AFP receptor antibodies or AFP into the patient to react with cancer cells in the patient if the testing indicates AFP receptors are present in the patient.

The present invention pertains to a method for treating cancer cells in a patient. The method comprises the steps of introducing modified AFP to cancer cells in the patient. Then there is the step of reacting the modified AFP with the AFP receptor of the cancer cells to inhibit growth of the cancer cells or kill the cancer cells.

It is the object of the invention to diagnose and follow up cancer diseases and pregnancy by detecting the alpha-fetoprotein receptor (AFP receptor) in bodily fluids and tissues. Even though the principles and methods are similar for detecting the AFP receptor in solution (bodily fluids) or attached to a solid matrix (tissue sections), they will be addressed separately for clarity purposes.

BRIEF DESCRIPTION OF THE DRAWINGS

In the accompanying drawings, the preferred embodiment of the invention and preferred methods of practicing the invention are illustrated in which.

DESCRIPTION OF THE PREFERRED EMBODIMENT

Figure 1:
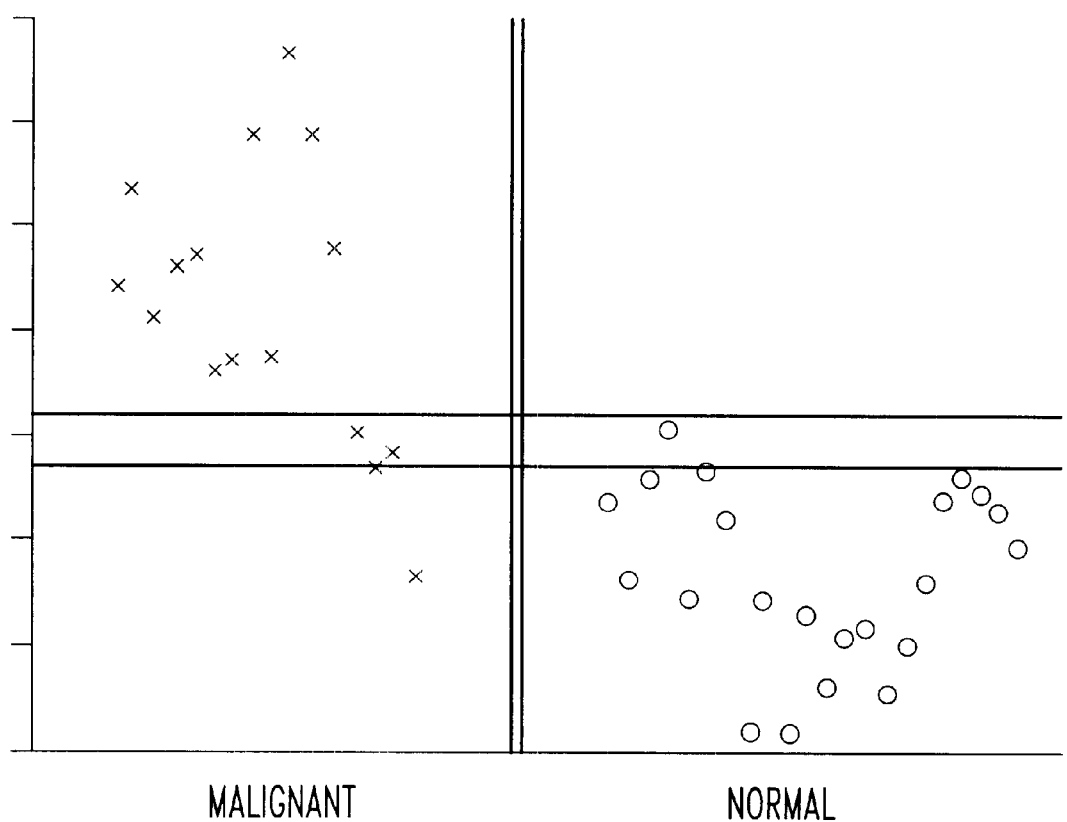
FIG. 1 is a chart of cancerous and nonmalignant diseases.
Figure 2:
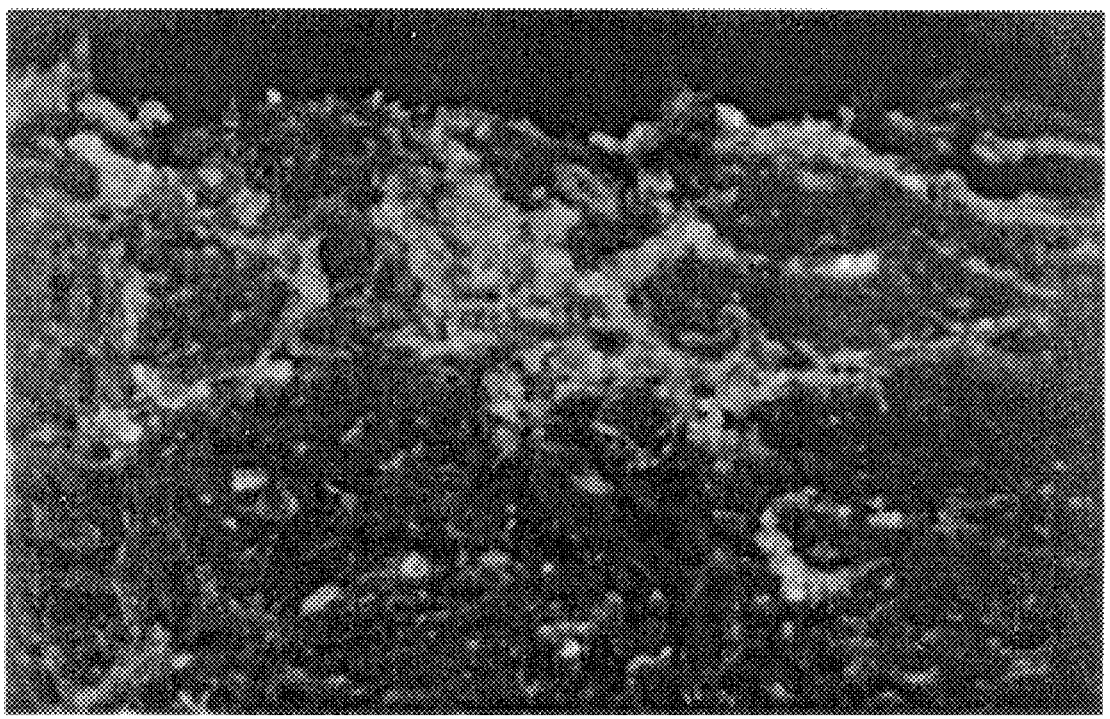
FIG. 2 is a computer generated illustration of a mammary carcinoma where the bright cells are cancerous.
Figure 3:
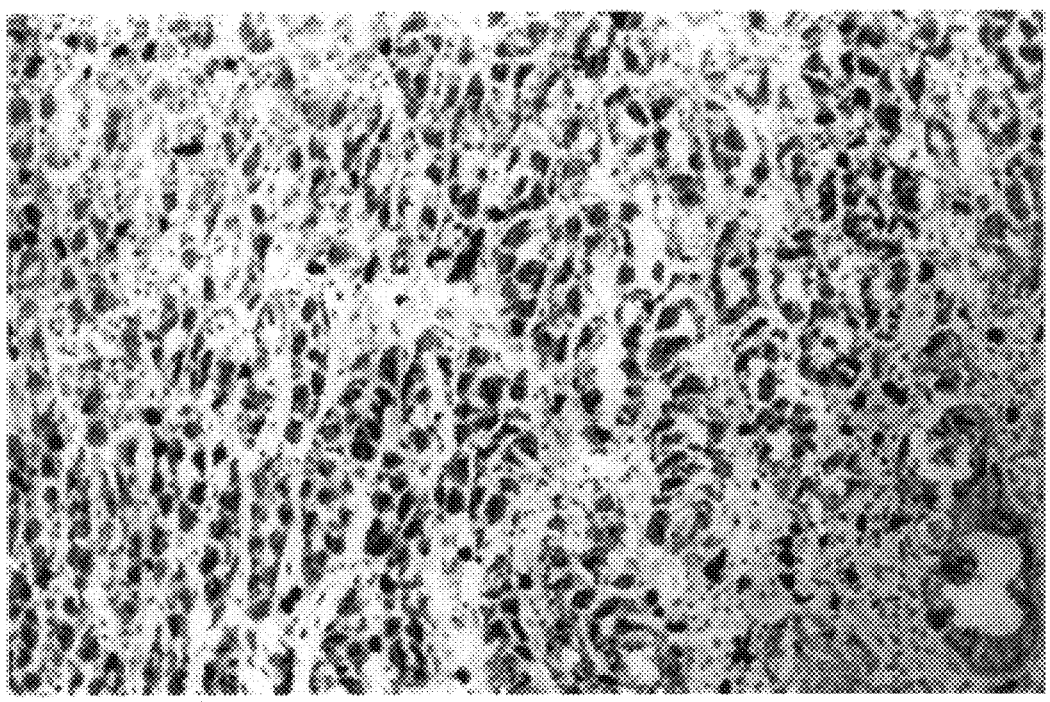
FIG. 3 is a computer generated illustration of a mammary carcinoma where the dark brown cells are cancerous.
Figure 4:
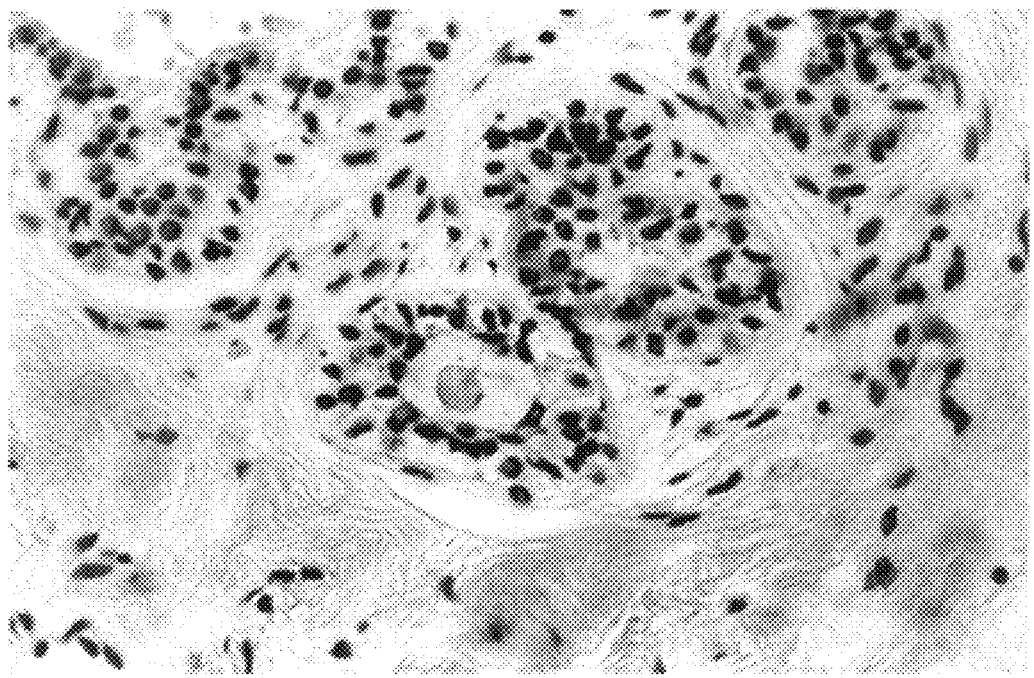
FIG. 4 is a computer generated illustration of a benign mammary adenoma.
Figure 5:
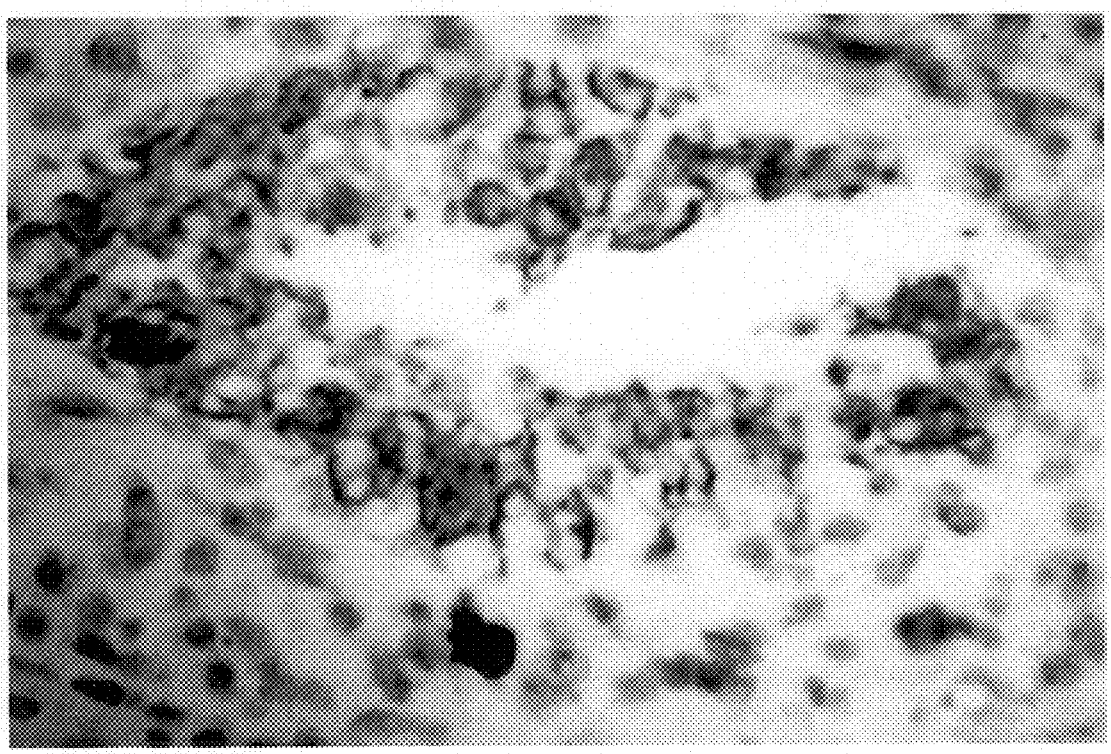
FIG. 5 is a computer generated illustration of lung carcinoma where the brown cells are cancer cells.
Figure 6:
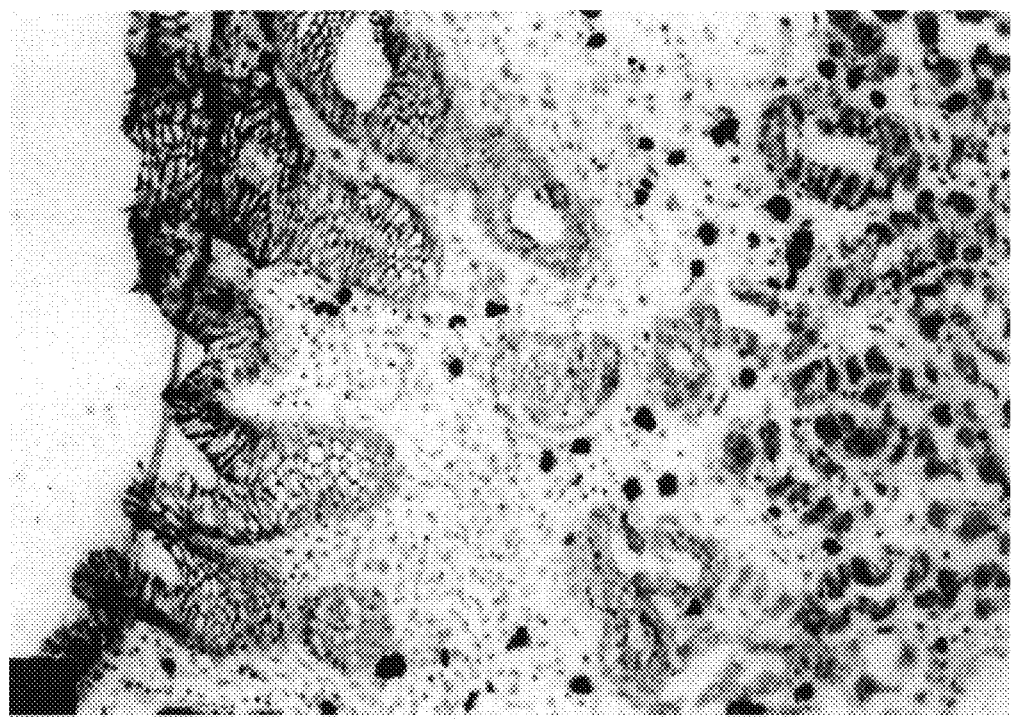
FIG. 6 is a computer generated illustration of a stomach cancer where the dark brown are cancer cells.

The present invention pertains to a method for detecting cancer in a patient. The method comprises the steps of introducing labeled antibodies or labeled AFP to a biological sample of the patient so the labeled antibodies or labeled AFP will react with the AFP receptor binding sites in the biological sample. The biological sample can be blood, saliva, tissue, serum, mucus, sputum, urine, or tears or material containing cancer cells. The biological sample can be a tissue section. The tissue section can be either fixed tissue, fresh tissue or frozen tissue. The antibodies can be monoclonal antibodies. The antibodies can be polyclonal antibodies. Next there is the step of identifying AFP receptor binding sites in the biological material which are reacted with the labeled antibodies or labeled AFP to determine the presence of cancer. Preferably, before the introducing step, there is the step of obtaining a biological sample from a body of a patient.

The introducing step can include the step of introducing antibodies labeled with radioisotope or AFP labeled with radioisotope to the biological sample of the patient so the labeled antibodies or labeled AFP will react with AFP receptor in the biological sample. The identifying step then includes the step of identifying the radioactivity present in the biological sample. More specifically, the identifying step can include the step of measuring a radioactive count of the biological sample. Or the identifying step can include the steps of coating the biological sample with a photographic emulsion, developing the photographic emulsion, and observing the biological sample with the coating. Alternatively, the biological sample is the patient and the introducing step includes the step of injecting the patient with antibodies labeled with radioisotope or AFP labeled with radioisotope.

In an alternative embodiment, the introducing step includes the step of introducing antibody labeled with an enzyme or AFP labeled with an enzyme to the biological sample of the patient so the labeled antibodies or labeled AFP will react with AFP receptor binding sites in the biological sample. The antibody labeled with enzyme or AFP labeled with enzyme change the color of the biological specimen, and the identifying step can include the step of comparing the color of the biological specimen with a known color to determine the presence of cancer. The enzyme can peroxidase, and the introducing step can include the step of introducing the antibody labeled with peroxidase to tissue of the patient. Alternatively, the introducing step can include the steps of placing a drop of the biological sample onto a location on nitrocellulose or nylon, and adding antibody labeled with peroxidase to the location. The identifying step then includes the step of determining whether the location on the nitrocellulose or nylon has changed color.

In another embodiment, the antibody labeled with enzyme or AFP labeled with enzyme release ions which change electrical conductance of solution in which the biological sample is disposed. The identifying step then includes the step of measuring the electrical conductance of the solution to determine the presence of cancer in the biological sample.

In yet another embodiment, the introducing step can include the step of introducing antibodies labeled with a fluorochrome or AFP labeled with a fluorochrome to the biological sample of the patient so the labeled antibodies or labeled AFP will react with AFP receptor in the biological sample. The identifying step then includes the steps of irradiating the biological sample with UV light, and measuring photon emission from the irradiated biological sample. As another example, the biological sample can be a smear of biological material containing cancer cells on a slide, and the identifying step includes the step of examining the smear with a microscope or by flurocytometry.

The present invention pertains to a method for treating cancer cells in a patient. The method comprises the steps of introducing AFP receptor antibodies to cancer cells in the patient. The antibodies can be monoclonal antibodies, polyclonal antibodies, antibodies from a species different than the patient, or antibodies produced in-vitro from lymphocytes of the same species as the patient. Then there is the step of reacting the AFP receptor antibodies with the AFP receptor of the cancer cells to inhibit growth of the cancer cells or kill the cancer cells.

The introducing step can include the step of injecting the AFP receptor antibodies into the patient. The injecting step can include the step of injecting through an IV into the patient's bloodstream the AFP receptor antibodies. Alternatively, the injecting step can include the step of injecting the AFP receptor antibodies into the patient at a location in proximity to the cancer cells.

Alternatively, the introducing step can include the step of vaccinating the patient against cancer cells. The vaccinating step can include the step of injecting AFP receptor of a species different than the patient into the patient to cause AFP receptor antibodies to be produced by the patient against the injected AFP receptor. The AFP receptor antibodies produced by the patient cross-react with AFP receptor or cancer cells in the patient.

The reacting step can include the step of reacting the AFP receptor of cancer cells in the patient with AFP receptor antibodies so the AFP receptor of the cancer cells are blocked or functionally impaired. Alternatively, the AFP receptor antibodies are AFP receptor antibodies which fix complement. Then the reacting step includes the step of reacting the AFP receptor antibodies which fix complement to the cancer cell so when complement chain reaction occurs, holes are punctured into the cancer cell's membrane which kill the cancer cell.

Alternatively, the AFP receptor antibodies are conjugated to drugs or toxins. Then, the reacting step includes the step of reacting the AFP receptor antibodies conjugated with drugs or toxins to the cancer cells so the cancer cells engulf the drugs or toxins into the cancer cells where enzymes of the cancer cells cut the drugs or toxins free from the antibodies causing the cells to be irreversibly damaged and killed.

In yet another alternative embodiment, the AFP receptor antibodies are radiolabelled. Then the reacting step includes the step of reacting the radiolabelled AFP receptor antibodies with cancer cells in the patient so radiation from the radiolabeled AFP receptor antibodies at a short distance from the cancer cell's DNA damages the DNA thus inducing death in the cancer cells.

The present invention pertains to a method for monitoring a patient. The method comprises the steps of treating the patient for cancer. Then there is the step of testing the patient at predetermined intervals after the treatment for AFP receptor levels.

The present invention pertains to a method for treating a patient. The method comprises the steps of testing the patient for AFP receptor. Then there is the step of introducing AFP receptor antibodies or AFP into the patient to react with cancer cells in the patient if the testing indicates AFP receptor are in the patient.

The present invention pertains to a method for treating cancer cells in a patient. The method comprises the steps of introducing modified AFP to cancer cells in the patient. The modified AFP is either synthetically produced or is a part of AFP. Then there is the step of reacting the modified AFP with the AFP receptor of the cancer cells to inhibit growth of the cancer cells or kill the cancer cells.

The introducing step can include the step of injecting the modified AFP into the patient. The injecting step can include the step of injecting through an IV into the patient's bloodstream the modified AFP. Alternatively, the injecting step includes the step of injecting the modified AFP into the patient at a location in proximity to the cancer cells.

The reacting step can include the step of reacting AFP receptor of cancer cells of the patient with modified AFP so the AFP receptor sites of the cancer cells are blocked or functionally impaired.

In general, except for the application or use of AFP, modified AFP or antibodies which react with AFP receptor, the above-described techniques are generally known to one skilled in the art.

Operation of the Invention

In Bodily Fluids

Either by secretion or by passive diffusion after cell death, the AFP receptor from cancerous or fetal/embryonic tissues can be released into the blood stream and from there into many other bodily fluids such as urine, tears, saliva, etc. The AFP receptor concentration in bodily fluids (including serum) would then be significantly different between healthy individuals and cancer or pregnant patients. This could in turn be used for diagnostic purposes. Also, the evolution of the concentration of AFP receptor in these bodily fluids can be used for follow-up purposes. For example: A patient is diagnosed with mammary adenocarcinoma and the serum concentration of AFP receptor is high. The patient is operated on and the tumor is removed. Subsequent AFP receptor determinations in serum show a sharp decrease immediately after surgery, followed by a plateau. However, six months later the concentration of AFP receptor in serum starts increasing again. This indicates a recurrence or metastases of the cancer which will likely precede the traditional clinical or other diagnostic methods. Alerted by an inexpensive test such as the one proposed the physician now looks for the malignant mass with more refined, expensive and if required, invasive methods.

In Tissue Samples

The AFP receptor is present in most cancer cells. Thus, it can be detected by immunohistological means or incubation with AFP suitably labeled (even though the latter has not been successfully used on paraffin sections, it works on frozen sections). On this basis, the diagnostic of malignancy can be made. In addition, by using fluorescein as a label, very few positive cells can be spotted on a tissue section.

This reduces the margin of error obtained with classic pathological analysis in which a few cancerous cells within an otherwise normal tissue might not be seen. Also, since the expression of AFP receptor is conditioned not to anatomical changes but differentiation and biochemical alterations, it is likely that cells that would otherwise look normal but are in fact in the early stages of tumorigenesis will appear as positive with a test to detect the AFP receptor.

Again, for clarity purposes, even though there is no difference in principle and only minor differences in the techniques used, the detection of AFP receptor in bodily fluids and in tissue sections will be addressed separately: Bodily Fluids

EXAMPLE #1

In one example, 22 serum samples from non-cancerous patients and 17 samples from cancerous patients were tested by an enzyme immuno-assay (EIA) for their AFP receptor concentration. The technique used was as follows: EIA 96 well plates were coated from 1 hour to overnight with serum samples from the above described groups diluted 1/16384 in phosphate buffered saline (PBS) (0.05 M PO4, 0.15 M NaCl, pH 7.5). Some wells were coated in a similar manner with the pleural effusion from a patient with lung metastases of a mammary carcinoma at a 1/256 dilution. This material, name coded P89 was used as a standard because of the large quantities available. This allowed P89 to be used as the same standard for comparing all the samples against all others in all the experiments. After 3 washes with PBS, non-specific binding sites were blocked with 1% ovalbumin or gelatin in PBS for 1 hour. After 3 washes, 100 ul of a 1/200 dilution in 1% ovalbumin in PBS of a monoclonal antibody (Mab) ascites produced in mice and directed against AFP receptor (Mab 167H.4 as described in (Moro, R., Tamaoki, T., Wegmann, T. G., Longenecker, B. M., and Laderoute, M. P. Tumour Biol. 14, 116 (1993)], incorporated by reference) was incubated in each well for 3 hours. Then the wells were washed 3 times with PBS and a commercial peroxidase-anti-mouse IgM conjugate was added at the concentration recommended by the supplier (Sigma Chemicals, S. Louis). After 1 hour, the plates were washed 3 times with PBS and the colour substrate for peroxidase (ABTS) was added at the concentration recommended by the supplier (Sigma). All incubations were done at room temperature. After 30 minutes, the optical density (O.D.) in each well was read at 405 nm using a standard Titertek plate reader. The results are expressed in Table I and FIG. 1.

TABLE I

|    | ORGAN    | TUMOR TYPE              |
|----|----------|-------------------------|
| 1  | Ovary    | Adenocarcinoma Mucin.   |
| 2  |          | Leukemia lymphoid       |
| 3  | Limb     | Agiosarcoma             |
| 4  | Uterus   | Adenocarcinoma          |
| 5  | Soft Tis.| Sarcoma                 |
| 6  | Ovary    | Adenocarcinoma Cystic   |
| 7  | Rectum   | Adenocarcinoma          |
| 8  | Pelvis   | Carcinomatosis          |
| 9  |          | Generally Spread Tumor  |
| 10 | Brain    | Astrocytoma             |
| 11 | Lung     | Neoplasia               |
| 12 | Liver    | Primary Hepatoma        |
| 13 | Pelvis   | Neoplasia               |
| 14 | Kidney   | Noeplasia (Metastatic)  |
| 15 | Colon    | Neoplasia               |
| 16 | Bone     | Osteosarcoma            |

The table shows the patient, type of tumor and ratio between the sample and P89 used as a standard throughout the study. The results indicate that all cancerous patients but one were positive when the threshold between positive and negative is set at 54% of P89. Noncancerous patients were all negative but one using the same threshold. An independent T-test reported the following values (using the data analysis in Excel (TM)):

| t-Test: Two-Sample Assuming Unequal Variances | | |
|---|---|---|
|  | Variable 1 | Variable 2 |
| Mean | 84.74571 | 33.26582 |
| Variance | 709.9173 | 300.2051 |
| Pearson Correlation |  | #N/A |
| Pooled Variance |  | 3.5 |
| df |  | 24.02215 |
| t |  | 6.758736 |
| P(T <= t) one-tail |  | 2.72E−07 |
| t Critical one-tail |  | 1.710882 |
| P(T <= t) two-tail |  | 5.44E−07 |
| t Critical two-tail |  | 2.063898 |

A 2 tail analysis yields a p=0.00000054, an extremely significant figure even for the small number of samples considered.

A patient (not present in the table) who was in the negative control group was positive. Alerted by the high significance of the data obtained, the physician in charge of this patient scanned her by CAT and found a tumor which happened to be a malignant hypernephroma. This malignancy was first detected by using this test and THEN confirmed clinically.

FIG. 1 shows the same results expressed as a graph in which the X axis has been split into 2 sections (malignant and non-malignant, the units are irrelevant) and the Y axis represents the percentage of P89 for each patient. The horizontal line represents the 54% +/− threshold.

EXAMPLE #2

In another embodiment, an adequate plastic or glass substrate (EIA plates or test tubes) is coated with monoclonal antibodies (Mab) against the AFP receptor at a suitable concentration. After washing out the excess of Mab, the substrate is blocked with an irrelevant protein or amino acid mixture to prevent non-specific binding and a suitable sample dilution of a patient bodily fluid (serum, saliva, urine, etc.) is incubated with the coated substrate for a suitable period of time. After washing to remove the unbound sample material, a second antibody, of the polyclonal type is added (polyclonal antibodies are produced by immunizing an animal and using its serum as the antibody source for the reaction as opposed to Mabs which are produced by individual clones of immortalized spleen cells in culture or grafted into a suitable host). This antibody can be conjugated to a suitable marker or enzyme to develop a colour or otherwise detectable reaction or the assay might proceed by adding an anti-second antibody marked with said label or enzyme. If the reaction involves this 3rd antibody, then the 2nd antibody should be produced in a different species than the 1st antibody and no cross reaction between the 1st and 3rd antibodies should be detectable. The reaction is then read by a suitable detector responding to the type of reaction developed (colour, conductivity, chemiluminescence, etc.).

EXAMPLE #3

Same as Example #2 but using two different polyclonal antibodies instead of a monoclonal and an antibody for the 1st and 2nd antibodies, respectively.

EXAMPLE #4

Same as Example #2 in which the substrate is a nitrocellulose or nylon membrane. The reaction is not measured by an apparatus but it is appears as a colour dot on the substrate. The reaction is considered as positive or negative with the naked eye.

EXAMPLE #5

Same as Example #3 in which the substrate is a nitrocellulose or nylon membrane. The reaction is not measured by an apparatus but it is appears as a colour dot on the substrate. The reaction is considered as positive or negative with the naked eye.

EXAMPLE #6

One of the antibodies in Examples #2–#5 is substituted by homologous or heterologous AFP which binds to the receptor.

EXAMPLE #7

KCI at concentrations over 0.4 M of KC1 dissociate the AFP receptor complex. This releases an additional amount of AFP receptor which might be undetectable since the recognition by one of the ligands (Mab, polyclonals or AFP) described in the previous examples might be impaired by the endogenous AFP that might be present in circulating AFP receptor complexes. As a result, the amount of AFP receptor might be increased thus increasing the sensitivity of the test. In this case, the sample might be treated with KC1 before or during incubation with the solid phase of the assay.

EXAMPLE #8

All of the above-mentioned examples in which the label is a radioactive compound (for radioimmuno assays and related techniques).

EXAMPLE #9

All of the above in which the reading of the assay is done by cheuriluminescence or fluorescence.

EXAMPLE #10

All of the above in which the reading is based on conductivity.
In Tissue Samples
The tissue sample can be obtained and processed in several ways:
Objection
(a) From organ samples removed by surgical procedures.
(b) Smears from secretions or other bodily fluids or by contact (PAP smears).
(c) From needle biopsy.
Processing of the Tissue Before Staining for AFP Receptor
The tissue samples can be fixed and cut, if necessary in a variety of ways:
  a) Frozen sections: The tissue is frozen solid before cutting. A fixative may or may not be used on these sections.
  b) Paraffin sections: In which the tissues are routinely processed in order to embed the sample in a paraffin block prior to cutting.
  c) Acrylic and other processes: Mainly for electronic microscopy processing.

EXAMPLE #11

Figure 7:
FIG. 7 is a computer generated illustration of an intestinal carcinoma.
Figure 8:
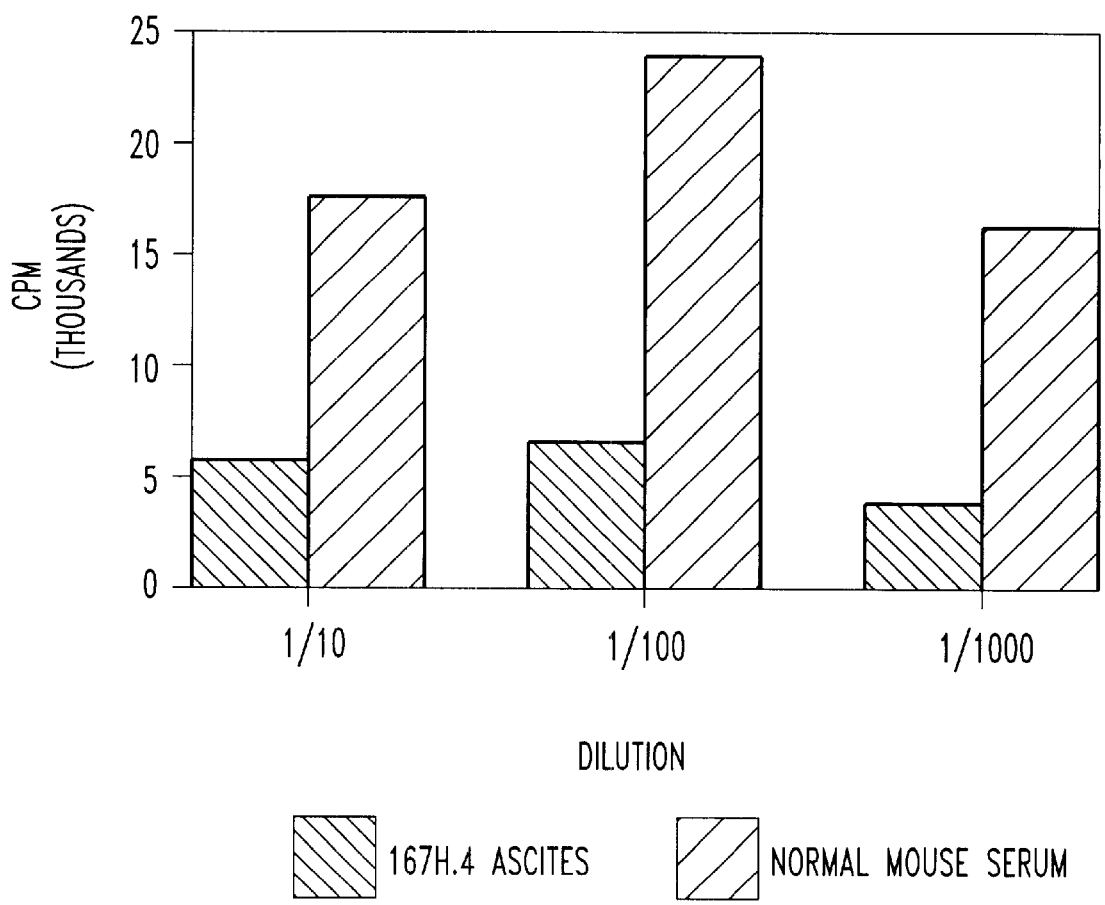
FIG. 8 is a graph showing P-388 growth inhibition by AFPr-1.

In this example, routine paraffin sections were used from a hospital department of pathology. The tissue was cut in 4–8 um thick sections. After rehydration, the sections were incubated with a solution of monoclonal antibody (Mab) ascites against the AFP receptor diluted 1:2000. Forty-five minutes later the slides were washed and incubated with an anti-mouse IgG+IgG peroxide or Rhodamine labeled conjugate. After 45 minutes, the sections were washed again and either observed under the microscope with a suitable light source or incubated with the peroxide substrate DAB until color was developed. The slides were then mounted routinely and observed under visible light. FIGS. 2–7 show computer generated illustrations of Rhodamine stained AFP receptor on mammary carcinomas (FIGS. 2–3), a benign mammary adenoma (FIG. 4), a lung carcinoma (FIG. 5), a stomach cancer (FIG. 6), and an intestinal carcinoma (FIG. 7). The figures show that cancer cells or cords or strips of cancer cells are positively stained whereas the non-malignant adjacent tissue is not. This is evident in FIG. 4 which shows a benign mammary adenoma. The cells are negative and there is no staining difference between the adenoma cells and the surrounding normal tissue.

Cancer Management

The expression of cancer markers on the surface of cancer cells entails the possibility to use them for cancer cell targeting for therapeutical purposes.

There are a number of ways to promote cell death by means of targeting surface antigens. For example, one can just use antibodies which fix complement. When the complement chain reaction happens, holes are punctured on the cell membrane which result in cell death. Another possibility is using anti-tumors antigen antibodies conjugated to drugs or toxins. Once attached to the cell surface, the conjugate is engulfed into the cell cytoplasm where cell enzymes cut the drugs or toxins free from the antibodies. Once released, the drugs or toxins damage the cell irreversibly inducing cell death. In another situation, radiolabelled antibodies can be used. Once stuck to the cells the radiation, at a short distance from the cell DNA, produces damage to the latter thus inducing cell death in the next replication.

The key component in all of the above procedures is the antibody which specifically recognizes malignant cells. If the (AFP receptor) is used as a cancer marker, then not only antibodies against it can be used as targeting molecules, but alpha-fetoprotein (AFP) itself will specifically recognize the AFP receptor. Thus, AFP can also be labeled with a variety of cytolytic agents to induce cell death.

In addition to destroying cancer cells, the latter can be induced to stop proliferating, as shown in the following example.

EXAMPLE #12

Figure 9:
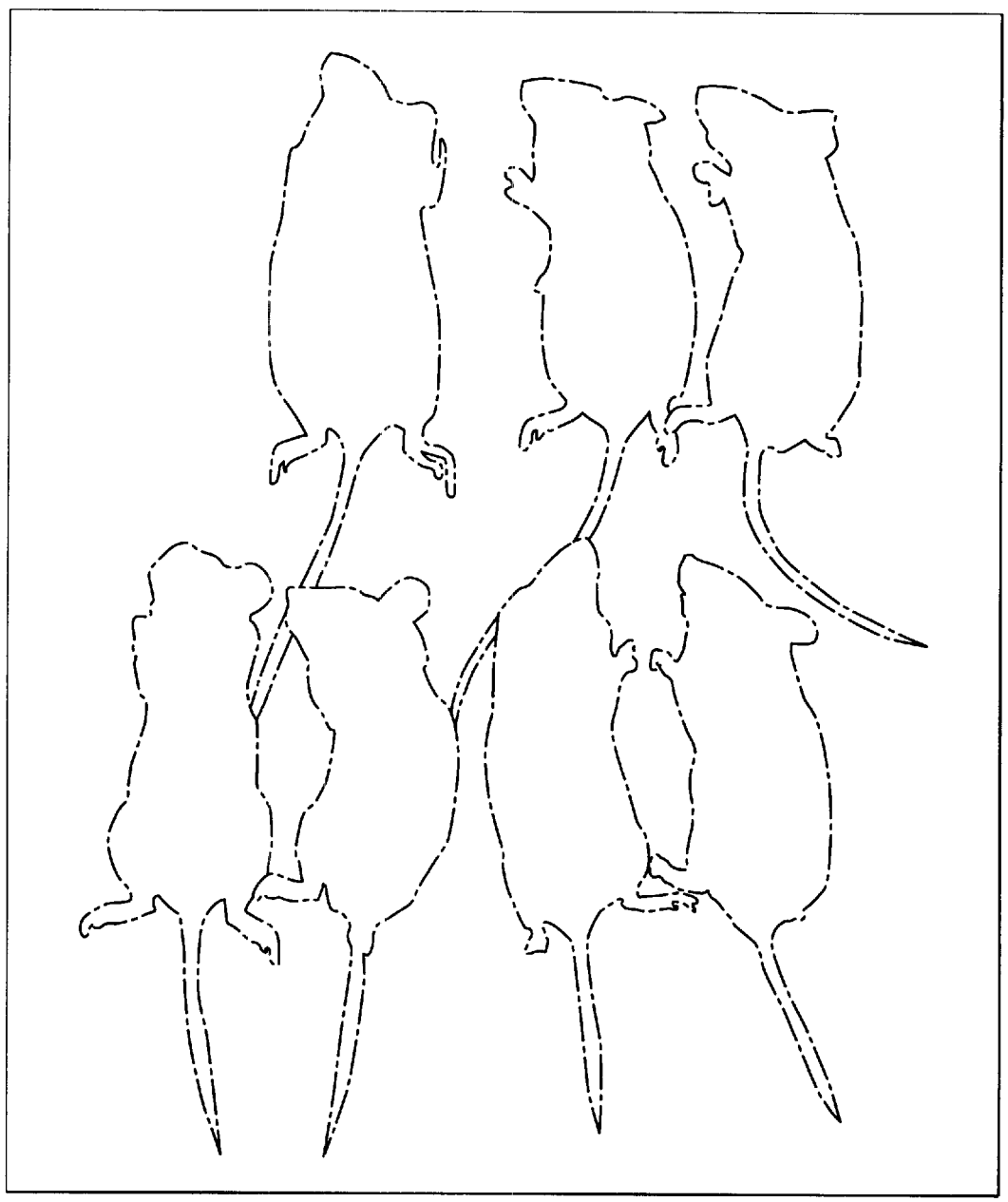
FIG. 9 is a drawing of three control animals on top and four treated animals after five days of injection.

P-388 mouse cells, expressing the AFP receptor, were incubated with different dilutions of a monoclonal antibody against AFP receptor. A complement fixation test was carried out previously and showed no cell destruction due to complement fixation. After 2–6 hours of inducation the P-388 cells were pulsed with $^3$H-Thymidine, washed and counted. FIG. 9 shows the radioactive thymidine counts of cells treated with the same concentration of AFPr-1 (an anti-AFP receptor monoclonal antibody) or normal mouse serum. As depicted, P388 proliferation can be greatly reduced by the Mab. Interestingly enough, when the cells are incubated for a few hours with the Mab and then washed and placed in culture again, their replication rate is very close to that of controls treated with irrelevant antibodies (normal mouse serum) thus indicating that the cells are not killed but inhibited from proliferating by the Mab. The proliferation inhibition in-vitro was also observed on the human LoVo digestive track cancer cell line (results not shown).

The reasons why cell proliferation is inhibited are not clear. A possible explanation is that AFP is believed, during fetal life, to carry fatty acids into fetal cells. These fatty acids are necessary for cells to synthesize membrane, a very active task during organogenesis. Since the extracellular concentration of AFP varies along time and from one tissue to another, it might be suicidal for a cell to enter into replication when the concentration of AFP surrounding it is inadequate. This concept supports the notion that the AFP receptor might serve as a messenger between the cell membrane and the nucleus. The antibody against the AFP receptor described in the experiments with P388 might somehow "jam" the message to the nucleus and therefore the cell does not go into division. This is important since there are other ways to "jam" the AFP receptor system using substances other than Mabs as will be discussed below.

An important consideration in this example and others is that mouse anti-AFP receptor monoclonal antibodies produced against human AFP receptor also recognize mouse cancer cells. A similar cross-reactivity between species was observed in binding studies when AFP from one species was incubated and bound to cells from a different species thus suggesting conformational similarities between the AFP receptors of different species.

EXAMPLE #13

Figure 10:
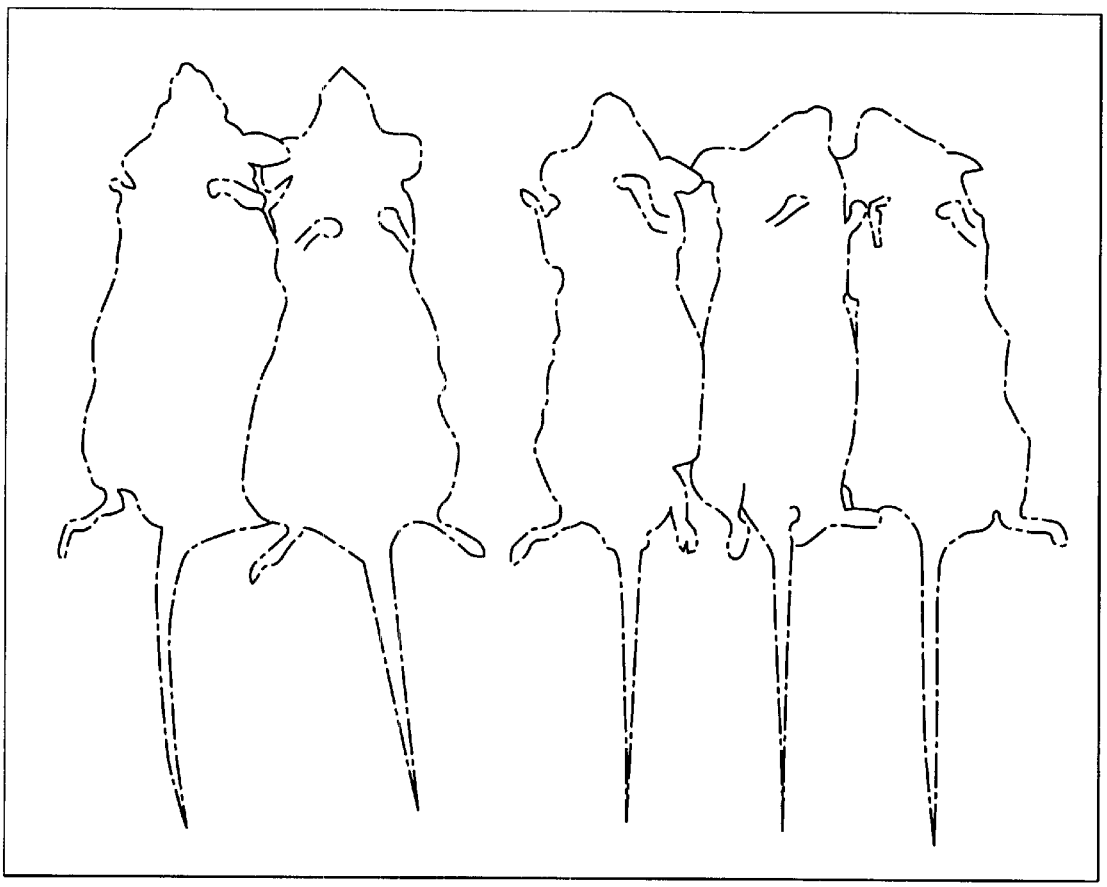
FIG. 10 shows a drawing of animals for another experiment in which three treated animals are free of disease and two bear large tumors.

C57 Black mice were simultaneously injected with $2 \times 10^6$ EL-4 cells subcutaneously on the abdomen and 100 ul of anti-AFP receptor ascites or normal mouse serum as a control into the tail veins. Due to a minor histo-incompatibility, the animals were irradiated with 300 rads. This helped the EL-4 cells take and produce tumors. The animals were observed for up to 21 days; sacrificed and photographed. FIGS. 9 and 10 show the results of two such experiments. FIG. 9 depicts 3 control animals on top (injected with normal mouse serum) and 4 treated animals on top (injected with normal mouse serum) and 4 treated animals after 5 days of injection. Tumors in the control group (some of them stained with a red felt to make them more apparent) were approximately 5 mm in diameter. Treated animals were free of disease (only a scar at the site of the injection could be observed). FIG. 10 shows a few animals from another experiment in which all 5 treated animals were free of disease (3 of which are shown) and 2 bear large tumors (the animals were sacrificed 15 days after the injections).

In another experiment, the treated animals were kept alive for 8 months without any signs of disease or abnormalities. Samples and bodily fluids. The AFP receptor is present on the cell membrane but also in the cytoplasm. As a matter of fact when radioactive AFP is incubated with cancer cells, approximately ⅔ of it is found in the cytoplasm, most likely associated to the AFP receptor. (reference 32. Naval, J., Villacampa, M. J., Goguel, A. F. and Uriel, J., Proc. Natl. Acad. Sci. U.S.A. 82, 3301 (1985) in the General Introduction I sent you). A method for purifying AFP receptor from human cord serum has been developed [Moro, R., Tamaoki, T., Wegmann, T. G., Longenecker, B. M., and Laderoute, M. P. Tumour Biol. 14, 116 (1993)], incorporated by reference. This method works because it is believed there is circulating AFP receptor liberated from dying cells or actively secreted by them. The fact is that AFP receptor is a soluble protein that is present in the blood of the newborn as one would expect.

The same happens in an individual with a tumor, only that the origin of AFP receptor are the malignant cells rather than the fetal cells in which it is expressed physiologically. Thus, there is AFP receptor in the tumor extracellular fluid. This is important because some bodily fluids or secretions can be directly obtained from that extracellular liquid. For example, a peritoneal carcinomatosis (cancer cells of any origin that metastasize the peritoneum and spread all over in the abdominal cavity) normally produces ascites fluid which we have tested and is rich in AFP receptor (do not confuse with the ascites induced in mice as a source of monoclonal antibodies, even though the physiopathological mechanisms are the same: cancer cells (in this case hybridomas producing monoclonal antibodies) in the peritoneal cavity create an inflammatory reaction which generates the ascites into which the hybridoma cells release the monoclonal antibody). P-89, which we have used as a reference standard in our enzyme immuno assays is the pleural effusion of a patient with lung metastases of a mammary carcinoma. The situation here is that cells from the mammary cancer migrated to the lung and started growing on the pleura, the membrane covering the lungs. The pleura reacts to cancer cells the same way the peritoneum does only that the liquid is called pleural effusion rather than ascites. In these cases (ascites and pleural effusion) the cancer cells which are in direct contact with the liquid (or floating in it) release the AFP receptor directly into it.

Ascites and pleural effusions are collected by puncture with a needle. In other cases, the secretion might come out the body spontaneously. For example, a bladder cancer might release AFP receptor in the urine which can then be monitored. A bronchial carcinoma might release AFP receptor in the mucus that can be collected as sputum by just forcing the patient to cough.

If the malignant cells are in close contact with the blood, as is the case in leukemias and some lymphomas, then the highest concentration of AFP receptor will be in serum.

All of the above are real situations, but not the most likely to happen. The most common cancers; stomach, mammary, uterus, colon and lung will release AFP receptor into the blood stream. This bodily fluid will exhibit the highest concentration of the marker in the fluids available for analysis. However, as the sensitivity of different immunochemical techniques increases, it might be possible to detect AFP receptor in other fluids. For example, a small amount of most of the serum proteins appears in saliva. It is obviously more practical to obtain a saliva sample than blood and if the amount of AFP receptor is high enough and the sensitivity of the reaction used is also enough, one might be able to use saliva instead of blood for diagnostic and follow-up purposes. The same follows for other bodily fluids.

In summary, in some cases it is convenient to use bodily fluids such as ascites, articular fluid (e.g. a bone cancer of a joint), pleural effusion, sputum, cerebrospinal fluid, urine, stool, etc. In other cases, blood or serum is the best choice. Finally, in some other cases it might be more convenient for practical or legal reasons to test other bodily fluids such as saliva or urine even though more AFP receptor might be present in serum. Bodily fluids can be collected from spontaneous secretions or by puncture with a suitable needle.

Immunochemical methods: These methods can be separated into 2 groups: the ones performed in a test tube or plate well in which the solid phase onto which the reaction is "stuck" is of an artificial nature and the one in which the solid phase is a natural portion of the host, for example, a tissue section or smear of blood cells. The formers are normally referred as immunochemical assays and the latter are called immunohistochemical (in the case of a tissue section) or immunocytochemical (when the cells are loose as in a smear) techniques. The principles are identical; the initial material is different. For the immunochemical assays, the molecule to be detected or measured must be in solution whereas in the immunohistochemical or immunocytochemical assays the molecule under scrutiny is part of a cell which is in the reaction.

The general principle of these reactions is simple: Antibodies (monoclonals or from serum or immunized animals) are very specific in the recognition of the structure against which they react. If an animal is immunized with a very pure fractions of say human albumin, its serum will ONLY recognize the albumin present in a sample which might also contain very large concentrations of hundreds of other proteins. Antibodies also have great affinity towards the substances they are created against (called antigens). Thus, very small amounts of these antigens can be detected.

The way immunochemical or immunohistochemical (immunocytochemical reactions are included with the latter since the only difference is that in one case, the cells are part of the structure of a tissue which was cut and placed on a slide and in the other case the cells are spread on the slide) reactions are carried out is the same: The substance (antigen) to be detected (here, the AFP receptor) is reacted with an antibody that is specific for that antigen. One of the two (the antibody or the antigen) is labeled (tagged) somehow. After incubating the two together, the excess reagent is washed out and the tag is put in evidence in a number of ways. If the tag is a radioisotope then the radioactive counts are measured with a suitable detector (normally, $^{125}I$ is used for these techniques and the gamma ray emission is measured. These techniques are grouped under the name of radioimmunoassay (RIA)). If the incubation with radioactive tag is done on a tissue section then $^3H$ is preferred and it is revealed on the slide after coating it with a photographic emulsion. Silver grains (black) appear where there is radioactivity. These grains can be observed under the microscope.

Another very popular technique uses an enzyme as the tag. An enzyme is a catalyzer and as such, it can convert a substrate into a new product. The interesting feature here is that 1 single enzyme molecule (such as horse radish peroxidase or alkaline phosphatase (the 2 mostly used)) can process 10,000 or more substrate molecules. Thus, the sensitivity becomes enormous since there is a 10,000 fold amplification factor. These reactions are known as enzyme-immunoassays (EIA) or enzyme linked immuno absorbent assays (ELISA). These enzymes usually produce a color change in the substrate. In soluble assays (immunochemical reactions) the solution in a test tube or a plate well changes color and therefore measuring the change one can quantitate the reaction (using a photocolorimeter or a spectrophotometer). In other cases, the enzyme releases ions from a non-ionic solution thus changing the electrical conductance of the solution which can then be measured electrically. In a variation of these techniques, the tag is biotin which is then recognized by avidin conjugated to the enzyme. The avidin-biotin reaction increases the overall sensitivity of the assay.

Recently, another type of tag was introduced. These tags are fluorochromes which upon being exited by UV light emit photons in the visible spectrum. The reactions are measured with a photocell immediately after exposure to a high intensity UV stimulating light pulse. These techniques are known as immunochemiluminesence.

Regardless of the way the molecules are tagged or the way the reactions are read, the reactions take place in a few well defined sequences described as follows:

Competition assays: In this case, free antigen (AFP receptor here) needs to be obtainable in relatively high quantities and in very pure form. The antibody (Ab) is attached to the solid phase (the test tube or plastic plate well or a suitable membrane, more on the latter below). The sample containing the antigen (Ag) is mixed with a known amount of pure tagged Ag. The mixture is incubated with the Ab on the solid phase. The more Ag in the original sample, the less tagged Ag can attach to a given amount of Ab on the solid phase (the Ag is in saturation compared to the amount of Ab). The reaction is quantitized by extrapolation against a solution containing a known amount of non-tagged Ag. This technique only works with soluble antigens, it is not useful for tissue samples. The main advantage competition assays have is that they require only one antibody.

Sandwich techniques: There are many variations: the traditional sandwich ELISA consists of chemically attaching one Ab to a solid phase. Then the sample containing the Ag to be measured is added. The dilutions are such that the reaction proceeds in excess of Ab. After incubation for a few minutes to a few hours, the excess reagents are washed out and a second antibody is added. This second antibody must recognize a site on the Ag molecule different from the one recognized by the first Ab. Otherwise, the site would be occupied by the 1st Ab and no reaction would occur (unless the Ag has more than 1 identical binding site that the 2 Ab's recognize, a rare instance). The 2nd Ab is also present in excess so that all of the Ag is recognized. This 2nd Ab is tagged. After washing again the reaction is read. Sandwich techniques have one advantage and that is that no pure Ag is necessary. The disadvantages are: More time for the reaction (minimum 2 incubations are necessary) and the need for 2 different antibodies.

The "one slice" sandwich is what was used in this example and what is used in most immunohistochemical reactions on tissues. Here, the Ag is fixed on the solid phase and the tagged Ab (only 1 Ab) is then incubated on it. The disadvantage, when using a test tube as the solid phase, is that the way the Ag sticks to the test tube might influence the intensity of the reaction and the "stickiness" might depend on other components in the sample which vary from one patient's serum to another (this is because the forces that bind the proteins to the glass or plastic on the test tube or plate well are electrostatic and weak in nature, as opposed to the strong reactions that bind an Ag to its Ab). To avoid this is that the double sandwich described above works with an excess of 1st Ab. Then, if the 1st Ab sticks to the solid phase more or less is irrelevant, there is always plenty, and there is no variation from one sample to another since the non-specific binding to the solid phase always use the same product in as assay (the 1st Ab preparation). The difference in the experiments between cancer and non-cancer patients here was such that they could not be explained by differences in the coating of the plastic plates used.

About the solid phase: This can be the tissue on a microscope slide or a suitable surface onto which the molecules will attach, usually by electrostatic forces (the preparation is usually just incubated for a few hours in the test tubes which are then washed. The proteins remain stuck to the glass or plastic). In some other case however, the solid phase might be a membrane usually made of nylon or nitrocellulose. These membranes are white. If once the membrane is coated with the Ag or Ab, then an assay similar to the one carried out on microscope tissue sections is carried out and the colour is developed using a substrate that rather than changing colour, generates a coloured precipitate, then at the end of the process, a colour spot indicates whether a reaction was positive or not. If there is colour, then there was reaction, if there is no colour the reaction was negative. This is an example of the "all or nothing" type of reaction mentioned before. It has the enormous advante it requires no apparatus to be read; the naked eye is enough. The major disadvantage is that it is not very precise.

Introduction of antibodies in the human body: There are several ways of having the patient's cancer cells exposed to anti-AFP receptor antibodies: One way is to inject purified mouse monoclonal antibodies (Mab) into the patient. If the malignant cells are in direct contact with the blood (e.g. leukemias) then the intravenous (I.V.) route is the choice. The same goes if the tumor is only accessible from the blood. There are some cases however where other routes might prove better. As mentioned above, some tumors grow in confined spaces such as the pleural cavity or the peritoneal cavity. In these cases, it might be better to inject the antibodies directly into the cavity rather than into the blood stream. Another way to getting antibodies against AFP receptor is by inducing them in the host. A cancer patient could be immunized with AFP receptor of a different species. Subtle differences between the conformation of the human and other species of receptors might allow to produce in that patient, antibodies which even though are directed against for example mouse or bovine AFP receptor, cross-react with the autologous human AFP receptor. Thus, the patient gets "vaccinated" against its own tumor. It is worth mentioning that antibodies are not the only way to jam the receptor on the surface of cancer cells. A denatured AFP could achieve the same purpose. Even a synthetic piece of AFP can obtain that result and therefore be useful to stop tumor growth.

There are several different ways of obtaining the modified AFP, either parts of the naturally occurring AFP or parts synthesized by molecular engineering from DNA. The key is the portion of the AFP which reacts with the AFP receptor is viable, but the remaining portion of the AFP is either not present or altered or damaged sufficiently to not be able to carry out its functionality. All of these ways are in and of themselves well known in the art. AFP is simply applied to each of these ways. They are, for instance, using a polypeptide synthesizer from, for example, Beckman Instruments to produce a synthetic part of AFP which reacts with the AFP receptor. The amino acid sequence corresponding to the part of the AFP that reacts with the AFP receptor is entered into the polypeptide synthesizer, and the synthesizer is activated. The synthesized polypeptide results. Alternatively, the AFP part can be synthesized with the introduction of the desired DNA sequence into a host system, via a suitable vector as is well known in the art. The host system then expresses the AFP part which is then collected and purified if desired. Or, transgenic synthesis can be utilized by placing the desired DNA sequence into, for instance, a fertilized bovine egg. The desired AFP part is then obtained from the animal after birth, as is well known in the art. See, for instance, Maniatis et al. (1982). Yet another way to obtain the desired AFP is by cutting naturally occurring AFP. The AFP is cleaved with a chain reagent such as cyanimid bromide and then purified to obtain the desired AFP part.

TABLE I

CANCER + PATIENTS

| Case # | Name | Sex | LOCALIZATION | FINAL DIAGNOSIS |
|---|---|---|---|---|
| 1 | J.G. | F | Soft Tis. | Sarcoma |
| 2 | O.R. | M | Bladder | Epithelioma |
| 6 | A.B. | F | Ovary | Adenocar Mucin. |
| 10 | M.S. | F |  | Leukemia lymphoid |
| 14 | M.B. | F | Limb | Agiosarcoma |
| 15 | G.B. | F | Uterus | Adenocarcinoma |
| 18 | J.E. | M | Soft Tis. | Sarcoma |
| 19 | S.F. | F | Ovary | Adenocarcinoma Cystic |
| 24 | E.G. | F | Rectum | Adenocarcinoma |
| 32 | M.C.O. | F | Pelvis | Carcinomatosis |
| 33 | E.M. | F | Abdomen | Gen. Spread Tumor |
| 34 | H.D.G | F | Brain | Astrocytoma |
| 35 | C.B | M | Lung | Neoplasia |
| 37 | R.F. | M | Liver | Primary Hepatoma |
| 67 | C.D. | M | Pelvis | Neoplasia |
| 68 | C.M. | F | Kidney | Neoplasia (Met) |
| 69 | U.D.S. | M | Colon | Neoplasia |
| 41 | J.B. | F | Bone | Osteosarcoma |

CANCER − PATIENTS

| Case # | Name | Sex | LOCALIZATION | FINAL DIAGNOSIS |
|---|---|---|---|---|
| 39 | H.T. | F | Lung | Vasc. hypoplasia |
| 40 | M.L. | F |  | Vascular disease |
| 58 | O.H. | M | Brain | Meningioma |
| 7 | S.R. | M | Lymph node | Imflamatory |
| 16 | S.C. | M | Liver | Cyrrosis |
| 21 | B.P. | M | Prostate | Adenoma |
| 29 | M.B. | F | Brain | Meningeal hemorrage |

-continued

| A | B | | C | D | E | F | G |
|---|---|---|---|---|---|---|---|
| 38 | 30 | H.A. | M | | Vascular disease | | |
| 39 | 44 | A.A. | M | | Vascular disease | | |
| 40 | 45 | J.F.T. | M | Brain | Ischemic accident | | |
| 41 | 46 | G.N. | M | Kidney | Malformation | | |
| 42 | 47 | H.P.P. | M | | Vascular disease | | |
| 43 | 48 | M.S. | F | | Vascular disease | | |
| 44 | 51 | B.O. | F | | Vascular disease | | |
| 45 | 53 | J.G. | M | | Hypertension | | |
| 46 | 54 | J.S. | M | | Hypertension | | |
| 47 | 55 | J.M. | M | | Normal | | |
| 48 | 56 | A.T. | M | | Vascular disease | | |
| 49 | 61 | F.D. | M | Brain | Meningeal hemmoragy | | |
| 50 | N1 | J.L.I | M | | Normal | | |
| 51 | N2 | E.V. | M | | Normal | | |
| 52 | N3 | F.F. | M | | Normal | | |

| | H | I | J | K |
|---|---|---|---|---|
| 1 | | | | |
| 2 | | | | |
| 3 | | | | |
| 4 | | | | |
| 5 | | | | |
| 6 | | O.D. Test/O.D. P-89 | | Below 54% |
| 7 | | As a percentage | | (considered as −) |
| 8 | | | | |
| 9 | | | | |
| 10 | 89 | | | − |
| 11 | 107 | | | − |
| 12 | 83 | | | − |
| 13 | 92 | | | − |
| 14 | 94 | MEAN | | − |
| 15 | 72 | 85 | | − |
| 16 | 74 | | | − |
| 17 | 118 | S.D. | | − |
| 18 | 74 | 26 | | − |
| 19 | 134 | | | − |
| 20 | 117 | Min | | − |
| 21 | 96 | 34 | | − |
| 22 | 61 | | | − |
| 23 | 54 | Max | | − |
| 24 | 56 | 134 | | − |
| 25 | 34 | | | + |
| 26 | | N = 16 | | |
| 27 | | | | |
| 28 | | | | |
| 29 | | | | <54 Neg |
| 30 | | | | |
| 31 | 47 | | | + |
| 32 | 32 | | | + |
| 33 | 52 | | | + |
| 34 | 62 | | | − |
| 35 | 29 | | | + |
| 36 | 54 | | | + |
| 37 | 44 | | | + |
| 38 | 3 | MEAN | | + |
| 39 | 28 | 33 | | + |
| 40 | 2 | | | + |
| 41 | 25 | S.D. | | + |
| 42 | 13 | 17 | | + |
| 43 | 21 | | | + |
| 44 | 23 | MAX | | + |
| 45 | 10 | 62 | | + |
| 46 | 20 | | | + |
| 47 | 32 | Min | | + |
| 48 | 48 | 2 | | + |
| 49 | 52 | | | + |
| 50 | 49 | N = 22 | | + |
| 51 | 46 | | | + |
| 52 | 38 | | | + |

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A method for detecting cancer in a patient comprising the steps of:

obtaining a biological sample selected from the group consisting of ovary, uterus, rectum, brain, liver, blood, serum and bone from the patient;

introducing, in vitro, labeled antibodies against alphafetoprotein receptor or labeled alphafetoprotein to said biological sample selected from the group consisting of ovary, uterus, rectum, brain, liver, blood, serum and bone of the patient so the labeled antibodies or labeled alphafetoprotein will react with alphafetoprotein receptor or alphafetoprotein receptor binding sites on the alphafetoprotein receptor for the labeled alphafetoprotein or the labeled antibody in said biological sample;

washing away uncomplexed labeled antibody against alphafetoprotein from said biological sample;

identifying alphafetoprotein receptor or alphafetoprotein receptor binding sites in said biological sample which have reacted with the labeled antibodies or labeled alphafetoprotein to determine the presence of cancer, wherein an increased level of alphafetoprotein receptor or alphafetoprotein receptor binding sites in relation to normal, non-malignant individuals indicates the presence of cancer.

2. A method as described in claim 1 wherein the introducing step includes the step of introducing antibodies labeled with radioisotope or AFP labeled with radioisotope to the biological sample of the patient so the labeled antibodies or labeled AFP will react with AFP receptor binding sites in the biological sample.

3. A method as described in claim 1 wherein the introducing step includes the step of introducing antibodies labeled with an enzyme or AFP labeled with an enzyme to the biological sample of the patient so the labeled antibodies or labeled AFP will react with AFP receptor binding sites in the biological sample.

4. A method as described in claim 1 wherein the introducing step includes the step of introducing antibodies labeled with a fluorochrome or AFP labeled with a fluorochrome to the biological sample of the patient so the labeled antibodies or labeled AFP will react with AFP receptor binding sites in the biological sample.

5. A method as described in claim 2 wherein the identifying step includes the step of identifying the radioactivity present in the biological sample.

6. A method as described in claim 5 wherein the identifying step includes the step of measuring a radioactive count from the biological sample.

7. A method as described in claim 5 wherein the identifying step includes the steps of coating the biological sample with a photographic emulsion, developing the photographic emulsion and observing the biological sample with the coating.

8. A method as described in claim 3 wherein the antibody labeled with enzyme or AFP labeled with enzyme change the color of the biological specimen, and the identifying step includes the step of comparing the color of the biological specimen with a known color standard.

9. A method as described in claim 8 wherein the enzyme is peroxidase.

10. A method as described in claim 8 wherein the introducing step includes the steps of placing a drop of the biological sample onto a location on nitrocellulose or nylon, and adding antibody labeled with peroxidase to the location, and the identifying step includes the step of determining whether the location on the nitrocellulose or nylon has changed color.

11. A method as described in claim 3 wherein the antibody labeled with enzyme or AFP labeled with enzyme release ions which change the electrical conductance of solution in which the biological sample is disposed, and the identifying step includes the step of measuring the electrical conductance of the solution.

12. A method as described in claim 4 wherein the identifying step includes the steps of irradiating the biological sample with UV light, and measuring photon emission from the irradiated biological sample.

13. A method as described in claim 1 wherein the antibodies are monoclonal antibodies.

14. A method as described in claim 1 wherein the antibodies are polyclonal antibodies.

15. A method as described in claim 1 wherein the biological sample is a tissue section.

16. A method as described in claim 1 wherein the biological sample is a smear of biological material containing cancer cells on a slide, and the identifying step includes the step of examining the smear with a microscope or by flurocytometry.

17. A method as described in claim 15 wherein the tissue section is from either fixed tissue, fresh tissue or frozen tissue.

* * * * *